(12) United States Patent
Johanson et al.

(10) Patent No.: US 8,221,998 B2
(45) Date of Patent: Jul. 17, 2012

(54) EXPRESSION OF PROTEIN GB1 DOMAIN FUSION PROTEINS IN MAMMALIAN CELLS

(75) Inventors: Kyung Oh Johanson, King of Prussia, PA (US); John J. Trill, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 979 days.

(21) Appl. No.: 11/914,953

(22) PCT Filed: May 19, 2006

(86) PCT No.: PCT/US2006/019872
§ 371 (c)(1),
(2), (4) Date: Jun. 9, 2008

(87) PCT Pub. No.: WO2006/127682
PCT Pub. Date: Nov. 30, 2006

(65) Prior Publication Data
US 2009/0148892 A1    Jun. 11, 2009

Related U.S. Application Data

(60) Provisional application No. 60/683,254, filed on May 20, 2005.

(51) Int. Cl.
*C12P 21/02* (2006.01)
*C12N 15/00* (2006.01)
*C12N 5/02* (2006.01)
*C12N 5/071* (2010.01)

(52) U.S. Cl. .................... 435/69.1; 435/70.1; 435/70.3; 435/320.1; 435/325

(58) Field of Classification Search .................. None
See application file for complete search history.

(56) References Cited

U.S. PATENT DOCUMENTS 5,965,390 A    10/1999  Bjorck et al.
6,663,862 B1 *  12/2003  Hellinga et al. ........... 424/133.1

FOREIGN PATENT DOCUMENTS

WO    WO 02/08263         1/2002
WO    WO 03100022 A2 *  12/2003
WO    WO 2005016956 A1 *  2/2005

OTHER PUBLICATIONS

Cockett et al. The use of engineered E1A genes to transactivate the hCMV-MIE promoter in permanent CHO cell lines. Nucleic Acids Research, vol. 19, No. 2, pp. 319-325, 1991.*
Ishida et al. Molecular cloning of nonsecreted endothelial cell-derived lipase isoforms. Genomics, vol. 83, pp. 24-33, Jan. 2004.*
Broedl et al. Endothelial lipase promotes the catabolism of ApoB-containing lipoproteins. Circulation Research, vol. 94, pp. 1554-1561, Apr. 29, 2004.*
Ross et al. Designed protein G core variants fold to native-like structures: Sequence selection by ORBIT tolerates variation in backbone specification. Protein Science, vol. 10, pp. 450-454, 2001.*
Du et al. Effects of segment substitution on the structure and stability of immunoglobulin G binding domain of streptococcal protein G. Biopolymers, vol. 79, pp. 9-17, Apr. 18, 2005.*
Cheng, et al., "An efficient system for small expression and refolding", *Biochemical and Biophysical Research Communications*, 317:2, 401-405 (2004).
Gronenborn, et al., "A novel, highly stable fold of the immunoglobulin binding domain of Streptococcal protein G", *Science*, vol. 253, pp. 657-661 (1991).
McDevitt, et al., "Endothelial lipase, lipoprotein lipase, and hepatic lipase: Expression, purification, and characterization", *Annual Meeting of the American Society for Biochemistry and Molecular Biology*, Boston, MA, Jun. 12-16, 2004. Abstract #15.25, printed as 1 page.

* cited by examiner

*Primary Examiner* — Jennifer Dunston
(74) *Attorney, Agent, or Firm* — Jonathan M. Dermott; William T. Han

(57) ABSTRACT

This present invention relates to the use of the B1 domain of Protein G as an epitope tag for over-expression of proteins in mammalian cells.

9 Claims, No Drawings

SEQUENCE LISTING

<160> NUMBER OF SEQ ID NOS: 8

<210> SEQ ID NO 1
<211> LENGTH: 56
<212> TYPE: PRT
<213> ORGANISM: Streptococcus

<400> SEQUENCE: 1

Asp Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 2
<211> LENGTH: 57
<212> TYPE: PRT
<213> ORGANISM: Streptococcus

<400> SEQUENCE: 2

Met Asp Thr Tyr Lys Leu Ile Leu Asn Gly Lys Thr Leu Lys Gly Glu
1               5                   10                  15

Thr Thr Thr Glu Ala Val Asp Ala Ala Thr Ala Glu Lys Val Phe Lys
            20                  25                  30

Gln Tyr Ala Asn Asp Asn Gly Val Asp Gly Glu Trp Thr Tyr Asp Asp
        35                  40                  45

Ala Thr Lys Thr Phe Thr Val Thr Glu
    50                  55

<210> SEQ ID NO 3
<211> LENGTH: 66
<212> TYPE: PRT
<213> ORGANISM: Streptococcus

<400> SEQUENCE: 3

Met Glu Ile Leu Ala Ala Leu Pro Lys Thr Asp Thr Tyr Lys Leu Ile
1               5                   10                  15

Leu Asn Gly Lys Thr Leu Lys Gly Glu Thr Thr Thr Glu Ala Val Asp
            20                  25                  30

Ala Ala Thr Ala Glu Lys Val Phe Lys Gln Tyr Ala Asn Asp Asn Gly
        35                  40                  45

Val Asp Gly Glu Trp Thr Tyr Asp Asp Ala Thr Lys Thr Phe Thr Val
    50                  55                  60

Thr Glu
65

<210> SEQ ID NO 4
<211> LENGTH: 168
<212> TYPE: DNA
<213> ORGANISM: Streptococcus

<400> SEQUENCE: 4
gacacttaca aattaatcct taatggtaaa acattgaaag gcgaaacaac tactgaagct      60
gttgatgctg ctactgcaga aaaagtcttc aaacaatacg ctaacgacaa cggtgttgac     120
ggtgaatgga cttacgacga tgcgactaag acctttacag ttactgaa                 168

<210> SEQ ID NO 5
<211> LENGTH: 171
<212> TYPE: DNA
<213> ORGANISM: Streptococcus

<400> SEQUENCE: 5
atggacactt acaaattaat ccttaatggt aaaacattga aaggcgaaac aactactgaa      60
gctgttgatg ctgctactgc agaaaaagtc ttcaaacaat acgctaacga caacggtgtt     120
gacggtgaat ggacttacga cgatgcgact aagacctta cagttactga a                171

<210> SEQ ID NO 6
<211> LENGTH: 198
<212> TYPE: DNA
<213> ORGANISM: Streptococcus

<400> SEQUENCE: 6
atggaaattt tagctgcatt acctaagact gacacttaca aattaatcct taatggtaaa      60
acattgaaag gcgaaacaac tactgaagct gttgatgctg ctactgcaga aaaagtcttc     120
aaacaatacg ctaacgacaa cggtgttgac ggtgaatgga cttacgacga tgcgactaag    180
acctttacag ttactgaa                                                    198

<210> SEQ ID NO 7
<211> LENGTH: 11
<212> TYPE: PRT
<213> ORGANISM: human

<400> SEQUENCE: 7

Ser Pro Val Pro Phe Gly Pro Glu Gly Arg Leu
 1               5                   10

<210> SEQ ID NO 8
<211> LENGTH: 14
<212> TYPE: PRT
<213> ORGANISM: human
<220> FEATURE:
<221> NAME/KEY: VARIANT
<222> LOCATION: 12
<223> OTHER INFORMATION: Xaa = Any Amino Acid

<400> SEQUENCE: 8

Ser Lys Gly Thr Ser His Glu Ala Gly Ile Val Xaa Arg Ile
 1               5                   10

EXPRESSION OF PROTEIN GB1 DOMAIN FUSION PROTEINS IN MAMMALIAN CELLS

This application is a national stage entry of International Application No. PCT/US2006/019872, filed 19 May 2006, which claims the benefit of U.S. Provisional Application No. 60/683,254, filed 20 May 2005.

FIELD OF INVENTION

This present invention relates to the use of the B1 domain of Protein G as an epitope tag for over-expression of proteins in mammalian cells.

BACKGROUND OF THE INVENTION

The immunoglobulin binding domain B1 of streptococcal protein G (herein sometimes referred to as GB1), as illustrated in Park, et al. *Biochemistry*, 36:14277-14283 (1997), is a small protein with a well developed hydrophobic core, that folds into a 4-stranded beta sheet with a flanking alpha helix. This protein contains no disulfides or free cysteines, no prolines or metal binding motifs. The GB1 is highly stable and soluble and is one of the most extensively used model systems in the area of protein folding and design.

In addition, the GB1 contains on its' surface binding sites for the C-terminal fragment of the heavy chain of immunoglobulin G (IgGFc). Proteins containing this domain can be purified by immobilized Fc, eluted from the affinity column by acid or proteolytically clipped off and detected by existing reagents.

It has been reported by Hammarstrom, et al. *Protein Sci.*, 11:313-321 (2002) comparing soluble expression levels of protein fusions with this B1 domain with fusions using MBP, NusA, ZZ, GST, Thioredoxin and His6 and 26 different proteins, that GB1 gave a higher percentage of soluble expressed proteins in *E. coli*. It has also been reported by Zhou, et al. *Journal of Biomolecular NMR*, 20:11-14 (2001) that when used as an epitope tag for fusion with *E. coli* expressed recombinant proteins, this domain does not need to be removed to obtain NMR structure. Finally, Cheng & Patel, *Biochem. Biophys. Res. Commun.*, 30:401-405 (2004) concluded that expression of GB1 containing proteins in *E. coli* increases expression levels.

In a majority of instances, because of protein folding and solubility issues, many recombinant proteins cannot be expressed in prokaryotic organisms. Therefore, mammalian cells are the expression system of choice for recombinant proteins needing extensive post-translation modifications. However, even with mammalian expression systems, low expression and low activity of the expressed recombinant proteins using small epitope tags, such as 6× Histidine and Strep-tag II, have negatively impacted large scale purification for crystallography and HIS. Data obtained from the expression of Endothelial Lipase indicated that with either no tag, with a 6× Histidine tag, or with a 6×Histidine/Strep-tag II, expression was very low, at levels >1 mg/liter.

It has been demonstrated that use of the IgGFc region as a tag leads to very high levels of protein expression. However, this tag can be detrimental to genes requiring a particular orientation such as a reverse dimer. They block proper folding and, thus, lead to loss of activity.

Thus, there remains a need for expression or overexpression of selected polypeptides in mammalian cells. It was totally unexpected to discover, in the instant invention, a dramatic increase in expression levels in mammalian cells using a GB1 tag over the traditionally used tags, and to see full activity in all of the proteins examined.

SUMMARY OF THE INVENTION

In one aspect, the present invention relates to a method for expression of a polypeptide (of interest) in a mammalian recombinant host cell comprising culturing the host cell comprising an expression vector comprising at least one GB1 polynucleotide directly or indirectly linked to a polynucleotide encoding the polypeptide of interest which produces the polypeptide under an appropriate culture condition and purifying such polypeptide.

In another aspect, the present invention provides polypeptides made by the above method.

In a further aspect, the invention relates to an expression vector, to be used in a mammalian recombinant host cell, comprising at least one GB1 polynucleotide directly or indirectly linked to a polynucleotide encoding the polypeptide for the production of the polypeptide.

Yet in further aspect, this invention relates to a mammalian recombinant host cell comprising an expression vector comprising at least one GB1 polynucleotide directly or indirectly linked to a polynucleotide encoding the polypeptide for producing the polypeptide.

DETAILED DESCRIPTION

As used herein "GB1 polypeptides" include isolated polypeptides comprising an amino acid sequence which has at least 70% identity, at least 80% identity, at least 90% identity, at least 95% identity, at least 97-99% identity, to that of SEQ ID NO:1, 2, or 3 over the entire length of SEQ ID NO:1, 2 or 3, respectively. Such polypeptides include those comprising the amino acid of SEQ ID NO: 1, 2 or 3.

```
                                              (SEQ ID NO: 1)
DTYKLILNGKTLKGETTTEAVDAATAEKVFKQYANDNGVDGEWT
YDDATKTFTVTE (SEQ ID NO: 2)
MDTYKLILNGKTLKGETTTEAVDAATAEKVFKQYANDNGVDGEW
TYDDATKTFTVTE (SEQ ID NO: 3)
MEILAALPKTDTYKLILNGKTLKGETTTEAVDAATAEKVEKQYAN
DNGVDGEWTYDDATKTFTVTE
```

Further, GB1 polypeptides include isolated polypeptides in which the amino acid sequence has at least 70% identity, at least 80% identity, at least 90% identity, at least 95% identity, at least 97-99% identity, to the amino acid sequence of SEQ ID NO:1, 2 or 3 over the entire length of SEQ ID NO:1, 2 or 3, respectively. Such polypeptides include the polypeptide of SEQ ID NO:1, 2 or 3.

Further, GB1 polypeptides include isolated polypeptides encoded by a polynucleotide comprising the sequence contained in SEQ ID NO:4, 5 or 6.

As used herein "GB1 polynucleotides" include isolated polynucleotides comprising a nucleotide sequence encoding a polypeptide which has at least 70% identity, at least 80% identity, at least 90% identity, at least 95% identity, to the amino acid sequence of SEQ ID NO:1, 2 or 3, over the entire length of SEQ ID NO: 1, 2 or 3, respectively. In this regard, polypeptides which have at least 97% identity, at least 98-99%, and at least 99% identity are also included. Such polynucleotides include a polynucleotide comprising the nucleotide sequence contained in SEQ ID NO:4, 5 or 6, encoding the polypeptide of SEQ ID NO: 1, 2 or 3, respectively, or a polynucleotide comprising the nucleotide sequence contained in SEQ ID NO: 4, 5, or 6 encoding the polypeptide of SEQ ID NO: 1, 2 or 3, respectively.

Further, polynucleotides of the present invention include isolated polynucleotides comprising a nucleotide sequence which has at least 70% identity, at least 80% identity, at least 90% identity, at least 95% identity, to SEQ ID NO: 4, 5 or 6 over the entire length of SEQ ID NO: 4, 5 or 6, respectively. In this regard, polynucleotides which have at least 97% identity, at least 98-99% identity, and at least 99% identity are included. Such polynucleotides include a polynucleotide comprising the polynucleotide of SEQ ID NO: 4, 5 or 6 as well as the polynucleotide of SEQ ID NO: 4, 5 or 6.

The invention also provides polynucleotides which are complementary to all the above described polynucleotides.

```
                                                (SEQ ID NO: 4)
gacact tacaaattaa tccttaatgg taaaacattg aaaggcgaaa caactactga agctgttgat gctgctactg cagaaaaagt cttcaaacaa tacgctaacg acaacggtgt tgacggtgaa tggacttacg acgatgcgac taagaccttt acagttactg aa (SEQ ID NO: 5)
atggacact tacaaattaa tccttaatgg taaaacattg aaaggcgaaa caactactga agctgttgat gctgctactg cagaaaaagt cttcaaacaa tacgctaacg acaacggtgt tgacggtgaa tggacttacg acgatgcgac taagaccttt acagttactg aa (SEQ ID NO: 6)
atggaa attttagctg cattacctaa gactgacact tacaaattaa tccttaatgg taaaacattg aaaggcgaaa caactactga agctgttgat gctgctactg cagaaaaagt cttcaaacaa tacgctaacg acaacggtgt tgacggtgaa tggacttacg acgatgcgac taagaccttt acagttactg aa
```

Polynucleotides which are complementary to all the above-described polynucleotides include, but are not limited to, any polynucleotide which will hybridize to SEQ ID NOs: 4, 5, or 6 under stringent conditions.

As herein used, the terms "stringent conditions" and a "stringent hybridization conditions" mean hybridization will occur only if there is at least 70% and at least 80%, at least 95% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403-410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:

1) Algorithm: Needleman and Wunsch, *J. Mol. Biol.* 48: 443-453 (1970)

Comparison matrix: BLOSSUM62 from Hentikoff and Hentikoff, *Proc. Natl. Acad. Sci. USA*. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol. Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:4, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:4 by the numerical percent of the respective percent identity (divided by 100) and subtracting that product from said total number of nucleotides in SEQ ID NO:4, or:

$$n_n \leq x_n - (x_n \cdot y),$$

wherein $n_n$ is the number of nucleotide alterations, $x_n$ is the total number of nucleotides in SEQ ID NO:4, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:1 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO: 1, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:1 by the numerical percent of the respective percent identity (divided by 100) and then subtracting that product from said total number of amino acids in SEQ ID NO:1, or:

$$n_a \leq x_a - (x_a \cdot y)$$

wherein $n_a$ is the number of amino acid alterations, $x_a$ is the total number of amino acids in SEQ ID NO:1, and y is, for instance 0.70 for 70%, 0.80 for 80%, 0.85 for 85% etc., and wherein any non-integer product of $x_a$ and y is rounded down to the nearest integer prior to subtracting it from $x_a$.

The term "expression vector" is used to denote a DNA molecule, linear or circular, that comprises a segment encoding a polypeptide (of interest) directly or indirectly fused to one or more GB1 polynucleotides operably linked to additional control sequences that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both. Some examples of suitable mammalian expression vectors are found in EP 307,247; 260,148; 309,237; and 307, 248.

Essentially any mammalian cell can be used in the invention. The cell can be a primary cell (e.g., a primary hepatocyte, primary neuronal cell, or primary myoblast) or it may be a cell of an established cell line. It is not necessary that the cell be capable of undergoing cell division; a terminally differentiated cell can be used in the invention. If desired, the virus can be introduced into a primary cell approximately 24 hours after plating of the primary cell to maximize the efficiency of infection. Preferably, the mammalian cell is a liver-derived cell, such as a HepG2 cell, a Hep3B cell, a Huh-7 cell, an FTO2B cell, a Hepa1-6 cell, or an SK-Hep-1 cell) or a Kupffer cell; a kidney cell, such as a cell of the kidney cell line 293, a PC12 cell (e.g., a differentiated PC12 cell induced by nerve growth factor), a COS cell (e.g., a COS7 cell), or a Vero cell (an African green monkey kidney cell); a neuronal cell, such as a fetal neuronal cell, cortical pyramidal cell, mitral cell, a granule cell, or a brain cell (e.g., a cell of the cerebral cortex; an astrocyte; a glial cell; a Schwann cell); a muscle cell, such as a myoblast or myotube (e.g., a $C_2 C_{12}$ cell); an embryonic stem cell, a spleen cell (e.g., a macrophage or lymphocyte); an epithelial cell, such as a HeLa cell (a human cervical carcinoma epithelial line); a fibroblast, such as an NIH3T3 cell; an endothelial cell; a WISH cell; an A549 cell; or a bone marrow stem cell. Other preferred mammalian cells include CHO/dhfr-cells, Ramos, Jurkat, HL60, and K-562 cells.

Mammalian cells can be transformed, for example, according to the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, 52, 456 (1973). Thus, the transformant transformed with the expression vector containing the polynucleotide encoding the polypeptide which will be expressed can be obtained.

Where mammalian cells are employed as the host, the transformant is cultivated in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30 to 40° C. for about 15 to 60 hours and, if necessary, the culture can be aerated or agitated.

The present invention also provides an expression vector comprising one or more GB1 polynucleotide directly or indirectly fused to a polynucleotide encoding a polypeptide of interest and related elements necessary for cellular expression of the protein encoded by a GB1 polynucleotide. For example, a promoter sequence that directs transcription of GB1 polynucleotide in a host cell can be incorporated into the expression vector.

As used herein "directly fused" means a GB1 polynucleotide is adjacent to a polynucleotide encoding a polypeptide of interest. However, "indirectly fused" means a GB1 polynucleotide is not adjacent to a polynucleotide encoding a polypeptide of interest, but rather there is one or more spacer, such as tobacco etch virus (TEV) protease cleavage site and/ or other tags (such as 6 Histidine epitope tag) is/are present between a GB1 polynucleotide and a polynucleotide encoding a polypeptide of interest. It should be important to emphasize GB1 can be placed before the 5' or after the 3' terminal of the polynucleotide encoding the polypeptide of interest.

As used herein "polypeptide of interest" refers to a polypeptide that will be expressed using a GB1 polypeptide as a tag. Polypeptides of interest, for example include Endothelial Lipase (EL) protein, Cholesterol Ester Transfer protein (CETp), etc.

For use in mammalian cells, the control functions on the expression vectors are often provided by viral material. For example, commonly used promoters are derived from the genomes of polyoma, Adenovirus2, retroviruses, cytomegalovirus, and Simian Virus 40 (SV40). Other promoters are those from heterologous sources, e.g., the beta actin promoter. The early and late promoters of SV40 virus are particularly useful because both are obtained easily from the virus as a fragment that also contains the SV40 viral origin of replication [Fiers et al., *Nature,* 273: 113 (1978)]. Smaller or larger SV40 fragments may also be used, provided there is included the approximately 250-bp sequence extending from the HindIII site toward the BglI site located in the viral origin of replication. The immediate early promoter of the human cytomegalovirus is conveniently obtained as a HindIII restriction fragment. Greenaway, et al., *Gene,* 18: 355-360 (1982). Further, it is also possible, and often desirable, to utilize promoter or control sequences normally associated with the desired gene sequence, provided such control sequences are compatible with the host cell systems.

Transcription of a DNA encoding a desired heterologous polypeptide (polypeptide of interest) by higher eukaryotes is increased by inserting an enhancer sequence into the vector. The enhancer is a cis-acting element of DNA, usually about from 10 to 300 bp that acts on a promoter to enhance its transcription-initiation activity. Enhancers are relatively orientation and position independent, having been found 5' [Laimins, et al., *Proc. Natl. Acad. Sci. USA,* 78: 993 (1981)] and 3' [Lusky, et al., *Mol. Cell. Bio.,* 3: 1108 (1983)] to the transcription unit, within an intron [Banerji, et al., *Cell.* 33: 729 (1983)] as well as within the coding sequence itself [Osborne, et al., *Mol. Cell. Bio.,* 4: 1293 (1984)]. However, the enhancer element may be located upstream of the promoter sequence for this invention. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in mammalian host cells can also contain polyadenylation sites. Examples of polyadenylation regions are those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell. If the vector is integrated into the host cell chromosome, the latter is often sufficient.

The expression vectors may suitably contain a selection gene, also termed a selectable marker. A selection gene encodes a protein necessary for the survival or growth of a host cell transformed with the vector. Examples of suitable selectable markers for mammalian cells include dihydrofolate reductase (DHFR), thymidine kinase (TK), or neomycin. When such selectable markers are successfully transferred into a mammalian host cell, the transformed mammalian host cell can survive if placed under selective pressure.

There are two widely used distinct categories of selective regimes. The first category is based on the metabolism of a cell and the use of a mutant cell line that lacks the ability to grow independent of a supplemented medium. Two examples are CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells that were not transformed with the DHFR or TK gene will not be capable of survival in non-supplemented medium. Therefore, direct selection of those cells requires cell growth in the absence of supplemental nutrients.

The second category is dominant selection, which refers to a selection scheme that does not require the use of a mutant cell line. This method typically employs a drug to arrest growth of a host cell. Those cells that have a novel gene would express a protein conveying drug resistance and would survive the selection. Examples of drugs used in dominant selection include neomycin [Southern and Berg, *J. Molec. Appl. Genet.,* 1: 327 (1982)], mycophenolic acid [Mulligan and Berg, *Science,* 209: 1422 (1980)], or hygromycin [Sugden, et al., *Mol. Cell. Biol.,* 5: 410-413 (1985)]. The three examples given above employ bacterial genes under eukaryotic control to convey resistance to the appropriate drug, i.e., neomycin (G418 or geneticin), xgpt (mycophenolic acid), or hygromycin, respectively.

As used herein, the term "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the DNA sequence of interest is capable of being transcribed and translated appropriately.

As used herein, the term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct expression thereof. Thus, for example, intervening untranslated yet transcribed sequences can be present between a promoter sequence and the coding sequence and the promoter sequence can still be considered "operably linked" to the coding sequence.

Furthermore, a nucleic acid coding sequence is operably linked to another nucleic acid coding sequence when the coding region for both nucleic acid molecules is capable of expression in the same reading frame. The nucleic acid sequences need not be contiguous, so long as they are capable of expression in the same reading frame. Thus, for example, intervening coding sequences, and the specified nucleic acid coding regions can still be considered "operably linked."

Thus, provided within the instant invention are methods for the expression of a polypeptide in a mammalian recombinant host cell comprising culturing the host cell under an appropriate condition, wherein said host cell comprises an expression vector comprising at least one GB1 polynucleotide directly or indirectly linked to the a polynucleotide encoding said polypeptide, and purifying such polypeptide. The polypeptide may be Cholesterol Ester Transfer protein or Endothelial Lipase. In some instances, the GB1 polynucleotide is SEQ ID NO: 4, 5, or 6. Said host cells may be Chinese Hamster Ovary cells. Certain Chinese Hamster Ovary cells may comprise the adenovirus E1A gene. In another aspect of the invention, host cells are COS or HEK cells.

In yet another aspect, at least one GB1 polynucleotide is linked directly or indirectly to the carboxy terminal of the polynucleotide encoding said polypeptide. At least one GB1 polynucleotide may be linked via a selective cleavage site to said polynucleotide encoding said polypeptide at the carboxy terminal. The selectable cleavage site may comprise tobacco etch virus protease cleavage site. In another aspect, methods are provided for cleaving said selectable cleavage site prior to purifying said polypeptide.

In another aspect of the present invention, expression vectors are provided for use in a mammalian recombinant host cell, comprising at least one GB1 polynucleotide directly or indirectly linked to a polynucleotide encoding a polypeptide for the production of said polypeptide.

In yet another aspect of the present invention, mammalian recombinant host cells are provided comprising an expression vector comprising at least one GB1 polynucleotide directly or indirectly linked to a polynucleotide encoding a polypeptide for the production of said polypeptide in said host cell.

Within this application, unless otherwise noted, the techniques utilized may be found in any of several well-known references such as Molecular Cloning: A Laboratory Manual (Sambrook, et al. 1989, Cold Spring Harbor Laboratory Press), Gene Expression Technology (Methods in Enzymology, Vol. 185 edited by D. Goeddel, 1991, Academic Press, San Diego, Calif.), "Guide to Protein Purification" in Methods in Enzymology (M. P. Deutscher, ed., (1990) Academic Press, Inc.); PCR Protocols: A Guide to Methods and Applications (Innis, et al. 1990. Academic Press, San Diego, Calif.), Culture of animal Cells: A Manual of Basic Technique, 2nd Ed. (R. I. Freshney, 1987. Liss, Inc. New York, N.Y.) Gene Transfer and Expression Protocols, pp. 109-128, ed. E. J. Murray, The Human Press Inc. Clifton, N.J.), and the Ambion Catalog (Ambion, Austin, Tex.).

The following examples are intended to illustrate specific embodiments now known for practicing the invention, but the invention is not to be considered limited thereto.

EXAMPLES

Cloning of GB1 Domain

In one embodiment a GB1 polynucleotide is a polynucleotide of SEQ ID NO: 4. The polynucleotide of SEQ ID NO: 4 was used in the following examples. Polynucleotide of SEQ ID NO: 4 was synthesized by conventional methods. To aid future clonings, for use as a C-terminal tag, an Asp718 restriction site was added to the 5' end of the gene and a stop codon with an Eco RV restriction site was added to the 3' end of the gene.

Example 1

Cloning and Stable Expression of Human Endothelial Lipase in CHO-E1A Cells

PCR primers were designed to add an Eco R1 restriction site to the 5' end of the Endothelial Lipase (EL) gene. The primer for the 3' end of the gene was designed to eliminate the stop codon, add a TEV protease cleavage site and introduce an Asp 718 restriction site.

These two fragments were ligated together with the vector pCDN, which was digested with EcoR1 and Eco RV, using standard techniques, to create pCDN-EL/TEV/GB1.

To create a stable cell line, the plasmid pCDN-EL-TEV-GB1, was linearized using the restriction enzyme Not 1 and electroporated into the CHO-E1A cell line, Acc-317, using the technique described in Hensley, et al. *J. Biol. Chem.*, 269:23949-23958 (1994). The cells were selected as a polyclonal population in 1×MR1-4 medium containing BSA without nucleosides. To provide medium for purification, the polyclonal cell line was scaled into 1.5 liters of 2×MR1-4 medium in a 3 liter bottle, 7.5×10E+5 cells/ml, at 34° C. for 7 days.

The Endothelial Lipase, EL/TEV/GB1 was purified as follows. The EL was captured from medium onto Fc resin (4 mg human Fc/ml NHS-activated Sepharose 4 Fast Flow; GE Healthcare). Fc resin was thoroughly washed with 25 mM sodium phosphate 0.15M sodium chloride 20% glycerol pH=7 and eluted with 0.1M triethylamine pH=11.6. Eluate was neutralized with 1M sodium phosphate pH=6. Yields were 0.9 mg total protein/ml Fc resin. Initial expression levels exceeded 20 mg/l.

Additionally, the plasmid pCDN-EL-TEV-GB1 was linearized using the restriction enzyme Not 1 and electroporated into the CHO-Lec-E1A cell line, Acc-1169. The cells were selected as a clonal population in 96 well plates using 1×MR1-4 medium containing BSA, nucleosides and 400 ug/ml G418 (Geneticin).

To provide medium for purification, a single clone was scaled into 2×MR1-4 medium with nucleosides in a 3 liter bottle, 7.5×10E+5 cells/ml, at 34° C. for 7 days. Post purification the protein was subjected to N-term analysis which yielded the sequence of SPVPFGPEGRL (SEQ ID NO: 7) and this matched the predicted sequence. MALDI-MS was also performed and the observed M.W., 56302 & 50468 (C-term truncate), matched the expected M.W., 56409. Endo H treatment at pH=7 was successful and after digestion full activity was maintained.

To determine activity of the enzyme, the purified EL-TEV-GB1 protein was assayed for phospholipase activity using PED 6 as a substrate.

Based on results from purification of a pCDN-EL-TEV-His construct, the above cell line makes approximately 27-fold more protein than the EL/His construct. Both of these constructs are active. Based on results from the purification of the EL-TEV-Fc construct, the Fc construct made approx 3 times more protein; however the Fc construct was inactive.

Example 2

Cloning and Stable Expression of Human CETP in CHO-E1A Cells

PCR primers were designed to add an Eco R1 restriction site to the 5' end of the human CETP (Cholesterol Ester Transfer protein) gene. The primer for the 3' end of the gene was designed to add a TEV protease cleavage site and introduce an Asp 718 restriction site.

PCR primers were generated to add an Asp 718 site on the 5' end of the GB1 domain and a 6× Histidine epitope tag, a stop codon followed by an Eco RV restriction site to the 3' end of the gene. These fragments were ligated together with the vector pCDN, which was digested with EcoR1 and Eco RV, using standard techniques, to create pCDN-CETP/TEV/GB1-His.

To create a stable cell line, the plasmid pCDN-CETP/TEV/GB1-His, was linearized using the restriction enzyme Not 1 and electroporated into the CHO-E1A cell line, Acc-317, using the technique described in Hensley, et al. *J. Biol. Chem.*, 269:23949-23958 (1994). The cells were selected in 96 well plates as a clonal population in 1×MR1-4 medium containing BSA without Nucleosides.

To determine activity of the various cell clones which arose, concentrated conditioned medium was assayed using the Cholesteryl Ester Transfer Protein Activity Assay Kit (Roar Biomedical, Inc.) with the rCETP standard supplied by Cardiovascular Targets, Inc. The results indicate that the protein is active.

To provide medium for purification, clone #15 was scaled into 2 liters of 2×MR1-4 medium with nucleosides in a 3 liter bottles, 7.5×10E+5 cells/ml, at 34° C. for 14 days. Conditioned medium was purified using a NiNTA resin column with a 30 mM imadazole wash followed by a 300 mM imadazole elution. The purification results indicate expression levels of about 2.5 mg/L. N-term analysis indicated a sequence of SKGTSHEAGIVXRI (SEQ ID NO:8), which is identical to the predicted sequence.

What is claimed:

1. A method for expressing a polypeptide in a mammalian recombinant host cell, said method comprising
culturing the host cell under an appropriate condition, wherein said host cell comprises an expression vector comprising at least one GB1 polynucleotide directly or indirectly linked to a polynucleotide encoding said polypeptide, wherein said at least one GB1 polynucleotide comprises SEQ ID NO: 6, and
purifying such polypeptide.

2. The method of claim 1, wherein said host cell is a Chinese Hamster Ovary cell.

3. The method of claim 1, wherein said host cell is a Chinese Hamster Ovary cell containing an adenovirus E1A gene.

4. The method of claim 1, wherein said host cell is a COS or HEK cell.

5. The method of claim 1, wherein said at least one GB1 polynucleotide is linked directly or indirectly to the 3' terminus of the polynucleotide encoding said polypeptide.

6. The method of claim 1, wherein said at least one GB1 polynucleotide is linked to said polynucleotide encoding said polypeptide via a polynucleotide encoding a selectable cleavage site.

7. The method of claim 6, wherein said selectable cleavage site comprises tobacco etch virus protease cleavage site.

8. The method of claim 6, further comprising cleaving said selectable cleavage site prior to purifying said polypeptide.

9. The method of claim 1 in which said polypeptide is Cholesterol Ester Transfer protein or Endothelial Lipase protein.

* * * * *